(12) United States Patent
Shinoda

(10) Patent No.: US 7,209,493 B2
(45) Date of Patent: Apr. 24, 2007

(54) MULTIPLEX TRANSMISSION SYSTEM AND MULTIPLEX TRANSMITTER

(75) Inventor: Hidetoshi Shinoda, Tokyo (JP)

(73) Assignee: NEC Corporation, Tokyo (JP)

( * ) Notice: Subject to any disclaimer, the term of this patent is extended or adjusted under 35 U.S.C. 154(b) by 1129 days.

(21) Appl. No.: 10/245,587

(22) Filed: Sep. 18, 2002

(65) Prior Publication Data

US 2003/0058888 A1   Mar. 27, 2003

(30) Foreign Application Priority Data

Sep. 26, 2001   (JP) .............................. 2001-293929

(51) Int. Cl.
  H04J 3/06   (2006.01)
  H04J 3/02   (2006.01)

(52) U.S. Cl. ...................... 370/510; 370/537; 370/542

(58) Field of Classification Search ................ 370/442, 370/466, 537, 542, 538, 543, 498, 503, 504, 370/510
See application file for complete search history.

(56) References Cited

U.S. PATENT DOCUMENTS

2003/0016697 A1* 1/2003 Jordan ........................ 370/466

* cited by examiner

Primary Examiner—Wing Chan
Assistant Examiner—Feben Micael Haile
(74) Attorney, Agent, or Firm—McGinn IP Law Group, PLLC

(57) ABSTRACT

A multiplex transmission system according to the invention includes a transmitter and a receiver. The transmitter is provided with an idle frame inserting unit that inserts a specific idle frame different from an idle frame inserted into a surplus band of another signal into a surplus band of a predetermined signal and generates an internal signal, a multiplexing unit that multiplexes internal signals by time division and generates a multiplexed signal and a framing unit that transmits the multiplexed signal to a transmission line interface. The receiver is provided with a frame synchronizing unit that establishes synchronization of a transmission line interface and detects a multiplexed signal acquired by multiplexing internal signals acquired by converting signals by time division, a channel identifying unit that detects the specific idle frame in the multiplexed signal and specifies a position multiplexed by time division of each internal signal based upon a position of the specific idle frame, a demultiplexing unit that demultiplexes the internal signals, an idle frame extracting unit that removes the idle frame from the internal signal and a channel processing receiving unit that restores the internal signal from which the idle frame is extracted to a signal.

20 Claims, 6 Drawing Sheets

MULTIPLEX TRANSMISSION SYSTEM AND MULTIPLEX TRANSMITTER

BACKGROUND OF THE INVENTION

1. Field of the Invention

The present invention relates to a multiplex transmission system that demultiplexes the following data into plural channels again after the multiplex transmission system multiplexes and transmits data received from plural channels, particularly relates to a system that multiplexes packets and others in an SDH/SONET frame and others by time division and transmits the frame and its equipment.

2. Description of the Related Art

For a multiplex transmission system that multiplexes packets received from plural channels and transmits them on a transmission line, there is a multiplex transmission system that multiplexes and transmits packets according to a packet multiplexing system. Generally, as the length of a packet is variable, the multiplex transmission system temporarily stores a packet received from each channel in a buffer, multiplexes it after the processing of a header and transmits it on a transmission line.

There is also a multiplex transmission system that multiplexes packets by time division and transmits them. Such a time-division multiplex transmission system multiplexes a packet received from each channel by time division and transmits it on a transmission line. In case data from plural channels are multiplexed in units of byte and are transmitted, a frame is generally generated and the data of each channel is multiplexed in order from a reference position of the frame.

In a multiplex transmission system according to a packet multiplexing system of these, to execute the processing of a packet the length of which is variable, a receive buffer that can temporarily store a packet having the maximum length is required every line. To control multiplexing, further large capacity is generally required for a transmission buffer. The transmission buffer means a buffer for storing a packet to be transmitted on a transmission line and the receive buffer means a buffer for storing a packet received from the transmission line.

In the meantime, in the multiplex transmission system according to the packet multiplexing system, as it is awaited to read a packet from a buffer to multiplex packets from plural channels on one transmission line, a delay of a packet fluctuates.

In the multiplex transmission system according to the packet multiplexing system, when packets from plural channels are multiplexed on one transmission line, blocking may occur.

As described above, though the multiplex transmission system according to the packet multiplexing system has an advantage that packets from plural channels different in a transfer rate can be effectively multiplexed, it also has problems that a buffer having large capacity is required, a delay fluctuates and blocking occurs.

Therefore, in case such problems are required to be avoided, the multiplex transmission system according to time-division multiplexing is preferable. Various interfaces different in a transfer rate and others can be housed in each channel by using a generic framing procedure (GFP) standardized based upon T1X1.5 for example for an interface in the multiplex transmission system according to time-division multiplexing.

The multiplex transmission system according to time-division multiplexing requires a frame on a transmission line, however, for a frame, there are two types of a frame defined on one's own terms and a standardized frame.

In a multiplex transmission system, a communication device may be required to be provided between a transmitter and a receiver of the multiplex transmission system because the distance of transmission is long.

In case a frame is defined on one's own terms, there is a problem that the existing communication device and a general-purpose communication device cannot be used between the transmitter and the receiver.

Therefore, in this type of multiplex transmission system, it is desirable that a worldwide standardized interface is used. For a worldwide standardized interface of a transmission line, there is a synchronous digital hierarchy/synchronous optical network (SDH/SONET). For a standardized interface such as SDH/SONET, a frame format is predetermined. In case a multiplex transmission system is defined as a system for multiplexing data of each channel in an SDH/SONET frame, a general-purpose communication device according to SDH/SONET can be used between a transmitter and a receiver.

In case data from plural channels is multiplexed in an SDH/SONET frame in units of byte for example by time division, it is required that a fragment of a payload is not used or data of each channel is multiplexed asynchronously with the SDH/SONET frame unless the number of channels is the number of channels in which data from the channels can be exactly multiplexed in a payload of one SDH/SONET frame.

In case data of each channel is multiplexed asynchronously with an SDH/SONET frame, a position in which data of each channel is multiplexed cannot be known based upon information shown in the form of an overhead and others of the SDH/SONET frame on the receive side.

In case a fragment of a payload is not used, a part of the payload becomes useless.

Recently, each chip vender provides chip set LSI that terminates an SDH/SONET frame, however, of them, there is chip set LSI which merely synchronizes in units of byte and does not output a signal showing a position in an SDH/SONET frame. In case such chip set LSI is used, a position of a multiplexed channel cannot be known on the receive side even if data of each channel is exactly multiplexed.

To enable the detection of a position of each channel multiplexed asynchronously with an SDH/SONET frame, a frame has only to be further generated every multiplexed channel in the SDH/SONET frame and fields for a synchronizing signal and a channel identifying signal have only to be provided in each frame. However, then, a band of each channel is reduced by quantity in which the fields for the synchronizing signal and the channel identifying signal are provided.

SUMMARY OF THE INVENTION

The object of the invention is to provide a time-division transmission system which uses a standard interface the frame configuration of which is predetermined and in which a band is not reduced for a synchronizing signal and a channel identifying signal.

The multiplex transmission system according to the invention is provided with a transmitter and a receiver. The transmitter converts a signal from each input channel to a frame of a predetermined internal interface, inserts a specific idle frame different from an idle frame inserted into a surplus band of a signal of another input channel into a surplus band of a signal of a predetermined input channel and generates an internal signal, multiplexes internal signals by time division, generates a multiplexed signal and transmits it to a transmission line interface. The receiver is synchronized with the transmission line interface, detects the multiplexed signal, detects the specific idle frame in the multiplexed signal, specifies a position multiplexed by time division of each internal signal based upon a position of the specific idle frame and demultiplexes each internal signal, removes the idle frame and the specific idle frame from each internal signal, restores the predetermined internal interface of each internal signal to the original interface and transmits each internal signal to each output channel.

Or the multiplex transmission system according to the invention is provided with first and second devices. The first device normally converts a signal from each input channel to a frame of a predetermined internal interface and generates each internal signal, multiplexes internal signals by time division and generates a multiplexed signal, transmits it to a transmission line interface, and when the first device receives a notice that a fault of a transmission line is detected from an opposite device via the transmission line interface, the first device inserts a specific idle frame different from an idle frame inserted in place of a signal of another input channel in place of a signal of a predetermined input channel. The second device is opposite to the first device via the transmission line interface, notifies the first device that a fault of a transmission line is detected when the fault is detected, is synchronized with the transmission line interface when the fault of the transmission line recovers and detects a multiplexed signal, detects a specific idle frame in the multiplexed signal, specifies a position multiplexed by time division of each internal signal based upon a position of the specific idle frame and demultiplexes each internal signal, removes the idle frame or the specific idle frame from each internal signal, restores the predetermined internal interface to the original interface and transmits each internal signal to each output channel.

The multiplex transmission system according to the invention is provided with a transmitter and a receiver. The transmitter converts a signal from each input channel to a frame of a predetermined internal interface, inserts a specific idle frame different from an idle frame inserted into a surplus band of a signal of another input channel into a surplus band of a signal of a predetermined input channel and generates an internal signal, multiplexes internal signals by time division, generates a multiplexed signal and transmits it to a transmission line interface. The receiver is synchronized with the transmission line interface, detects the multiplexed signal, detects the specific idle frame in the multiplexed signal, specifies a position multiplexed by time division of each internal signal based upon a position of the specific idle frame and demultiplexes each internal signal, removes the idle frame and the specific idle frame from each internal signal, restores the predetermined internal interface to the original interface and transmits each internal signal to each output channel.

Or the multiplex transmission system according to the invention is provided with a transmitter and a receiver. The transmitter normally converts a signal from each input channel to a frame of a predetermined internal interface and generates each internal signal, multiplexes internal signals by time division and generates a multiplexed signal and transmits the multiplexed signal to a transmission line interface, and when the transmitter receives a notice that a fault of a transmission line is detected from an opposite device via the transmission line interface, the transmitter inserts a specific idle frame different from an idle frame inserted in place of a signal of another input channel in place of a signal of a predetermined input channel. The receiver notifies the opposite transmitter that a fault of the transmission line is detected when the receiver detects the fault, is synchronized with the transmission line interface when the fault of the transmission line recovers, detects the multiplexed signal, detects the specific idle frame in the multiplexed signal, specifies a position multiplexed by time division of each internal signal based upon a position of the specific idle frame and demultiplexes each internal signal, removes the idle frame or the specific idle frame from each internal signal, restores the predetermined internal interface to the original interface and transmits each internal signal to each output channel.

The multiplex transmission system according to the invention is provided with an idle frame inserting unit that inserts a specific idle frame different from an idle frame inserted into a surplus band of another signal into a surplus band of a predetermined signal and generates an internal signal, a multiplexing unit that multiplexes internal signals by time division and generates a multiplexed signal and a framing unit that transmits the multiplexed signal to a transmission line interface.

The multiplex transmission system according to the invention is provided with a frame synchronizing unit that is synchronized with a transmission line interface and detects a multiplexed signal acquired by multiplexing internal signals acquired by converting signals by time division, a channel identifying unit that detects a specific idle frame in the multiplexed signal and specifies a position multiplexed by time division of each internal signal based upon a position of the specific idle frame, a demultiplexing unit that demultiplexes each internal signal, an idle frame extracting unit that removes an idle frame from each internal signal and a channel processing receiving unit that restores the internal signal from which the idle frame is extracted to a signal.

BRIEF DESCRIPTION OF THE DRAWINGS

The above and other objects, features and advantages of the present invention will become more apparent from the following detailed description when taken in conjunction with the accompanying drawings, wherein.

DETAILED DESCRIPTION OF THE PREFERRED EMBODIMENTS

First Embodiment

Figure 1:
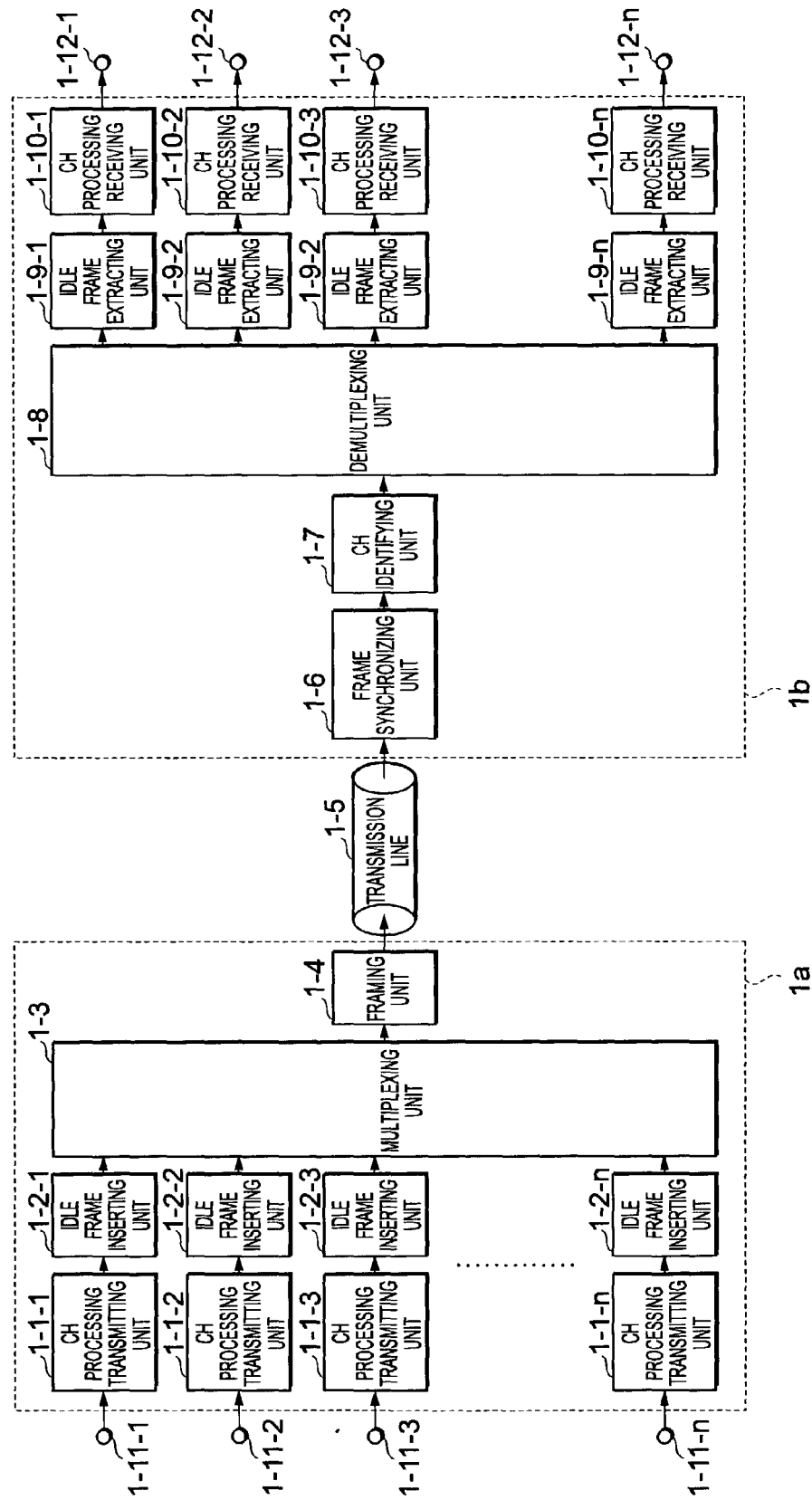
FIG. 1 is. a block diagram showing the configuration of a multiplex transmission system equivalent to a first embodiment of the invention.

Referring to the drawings, a first embodiment of the invention will be described in detail below.

FIG. 1 is a block diagram showing the configuration of a multiplex transmission system equivalent to the first embodiment. As shown in FIG. 1, the multiplex transmission system equivalent to this embodiment is configured by a transmitter 1a and a receiver 1b. The transmitter 1a and the receiver 1b are connected via a transmission line 1-5.

The transmitter 1a converts signals received from input channels 1-11-1, 1-11-2, - - -, 1-11-n to frames according to a generic framing procedure (GFP) standardized based upon T1X1.5, multiplexes the frames by time division after an idle frame is inserted and transmits them as an SDH/SONET frame via the transmission line 1-5. Signals from the input channels 1-11-1, 1-11-2, - - -, 1-11-n are Ethernet frames for example.

The transmitter 1a is composed of channel processing transmitting units 1-1-1. 1-1-2, - - -, 1-1-n, idle frame inserting units 1-2-1, 1-2-2, - - -, 1-2-n, a multiplexing unit 1-3 and a framing unit 1-4.

The channel processing transmitting units 1-1-1, 1-1-2, - - -, 1-1-n convert a signal respectively received from the input channels 1-11-1, 1-11-2, - - -, 1-11-n corresponding to the respective units to a GFP frame.

The idle frame inserting units 1-2-1, 1-2-2, - - -, 1-2-n receive a signal respectively converted to the GFP frame in the channel processing transmitting units 1-1-1, 1-1-2, 1-1-n corresponding to the respective units and insert an idle frame into a part which is not the GFP frame. However, only the idle frame inserting unit 1-2-1 inserts an idle frame for a reference channel different from the other idle frame inserting units 1-2-2, - - -, 1-2-n. Hereby, the channel into which the idle frame inserting unit 1-2-1 inserts the idle frame for the reference channel functions as a reference channel for identifying a multiplexed position of each channel.

The multiplexing unit 1-3 receives a signal filled with a frame of effective data according to GFP (hereinafter called an effective frame) and an idle frame from each idle frame inserting unit 1-2-1, 1-2-2, - - -, 1-2-n and multiplexes them in units of byte by time division.

The framing unit 1-4 generates an-SDH/SONET frame, inserts a signal multiplexed by time division by the multiplexing unit 1-3 into its payload and transmits the frame via the transmission line 1-5. SDH/SONET is an example of an interface the format of which is predetermined and the invention is not limited to this.

The receiver 1b receives an SDH/SONET frame in which plural signals are multiplexed by time division from the transmission line 1-5, extracts its payload, demultiplexes the payload every channel after a reference channel is detected from an idle frame and transmits each to output channels 1-12-1, 1-12-2, - - -, 1-12-n.

The receiver 1b is composed of a frame synchronizing unit 1-6, a channel identifying unit 1-7, a demultiplexing unit 1-8, idle frame extracting units 1-9-1, 1-9-2, - - -, 1-9-n and channel processing receiving units 1-10-1, 1-10-2, - - -, 1-10-n.

The frame synchronizing unit 1-6 synchronizes with an SDH/SONET frame and specifies a position of its payload.

The channel identifying unit 1-7 detects a multiplexed position of the reference channel in the payload based upon the idle frame and specifies a position of each channel.

The demultiplexing unit 1-8 demultiplexes each channel in the position specified by the channel identifying unit 1-7.

The idle frame extracting units 1-9-1, 1-9-2, - - -, 1-9-n extract the idle frame from a signal of each channel demultiplexed by the demultiplexing unit 1-8.

The channel processing receiving units 1-10-1, 1-10-2, - - -, 1-10-n receive an effective frame from the idle frame extracting units 1-9-1, 1-9-2, - - -, 1-9-n corresponding to the respective units, respectively convert it to an Ethernet frame and transmit the Ethernet frame to output channels 1-12-1, 1-12-2, - - -, 1-12-n corresponding to the respective units.

In the multiplex transmission system equivalent to this embodiment, as a signal between the units in the system is a GFP frame, a signal on the input channel and the output channel is not limited to an Ethernet frame and maybe signals of various formats. In that case, the channel processing transmitting units 1-1-1, 1-1-2, - - -, 1-1-n and the channel processing receiving units 1-10-1, 1-10-2, - - -, 1-10-n respectively for converting between a signal on the channel and a GFP frame have only to be made to correspond to a signal on each channel.

Figure 2:
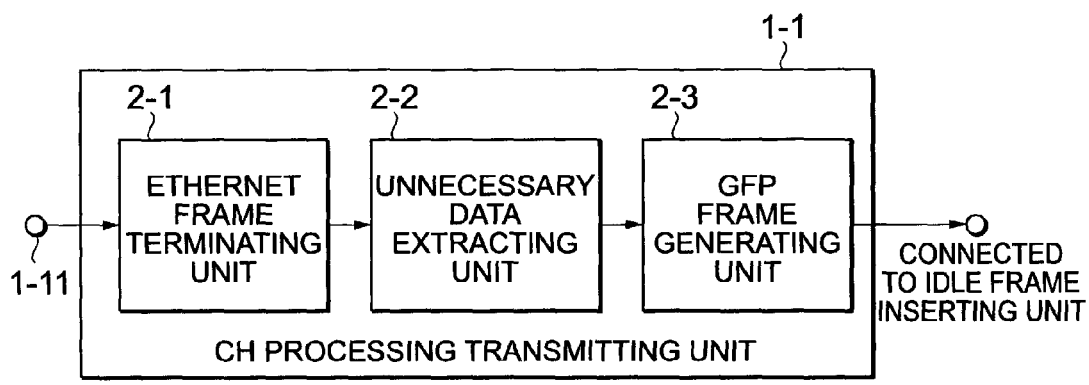
FIG. 2 is a block diagram showing the configuration of a channel processing transmitting unit in case a signal on an input channel is an Ethernet frame.

FIG. 2 is a block diagram showing the configuration of the channel processing transmitting unit in case a signal on each input channel is an Ethernet frame. As shown in FIG. 2, the channel processing transmitting unit 1-1 is composed of an Ethernet frame terminating unit 2-1, an unnecessary data extracting unit 2-2 and a GFP frame generating unit 2-3.

The Ethernet frame terminating unit 2-1 terminates an Ethernet frame received from the input channel 1-11 and extracts data in each field. The unnecessary data extracting unit 2-2 extracts unnecessaries from the data extracted by the Ethernet frame terminating unit 2-1. The GFP frame generating unit 2-3 generates a GFP frame using necessary data.

Figure 3:
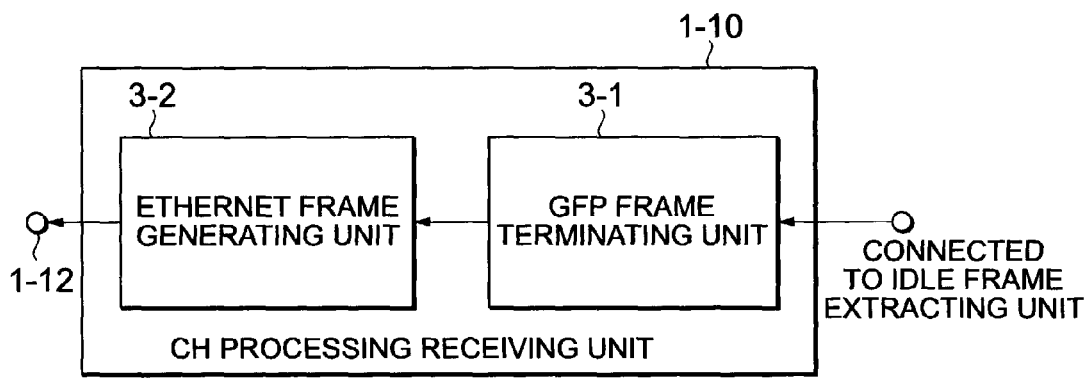
FIG. 3 is a block diagram showing the configuration of a channel processing receiving unit in case a signal on an output channel is an Ethernet frame.

FIG. 3 is a block diagram showing the configuration of the channel processing receiving unit in case a signal on the output channel is an Ethernet frame. As shown in FIG. 3, the channel processing receiving unit 1-10 is composed of a GFP frame terminating unit 3-1 and an Ethernet frame generating unit 3-2.

The GFP frame terminating unit 3-1 detects a GFP frame and extracts necessary data from each field. The Ethernet frame generating unit 3-2 generates an Ethernet frame using the necessary data extracted by the GFP frame terminating unit 3-1.

Figure 4:
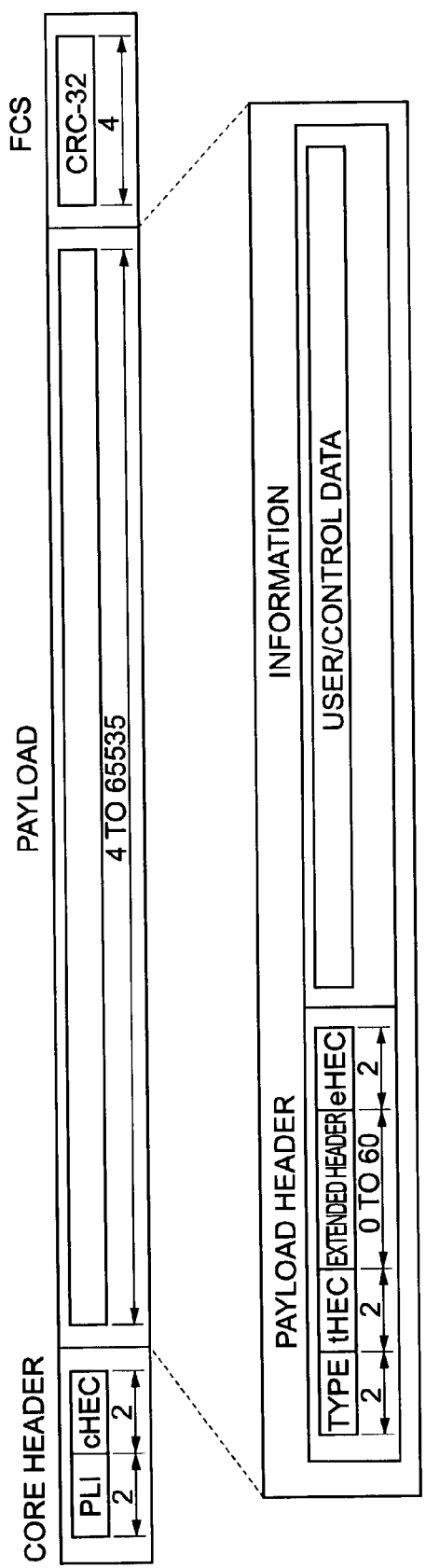
FIG. 4 shows a format of an effective frame according to GFP.

FIG. 4 shows a format of an effective frame according to GFP. As shown in FIG. 4, the effective frame is composed of each field of a core header, a payload and FCS.

The core header includes PLI and cHEC. A PDU length indicator (PLI) is a field for a physical layer identifier. Core header error control (CHEC) is a field for error detection and the establishment of synchronization of the core header.

The payload includes a payload header and an information division.

The payload header further includes each field of a payload type, tHEC, an extended header and eHEC. The payload type is a field showing the type of the payload. Type header error control (tHEC) is a field used for the error detection of the payload type. The extended header is a header including data required for processing the payload. Extended header error control (eHEC) is a field used for the error detection of the extended header. The information division is different depending upon the payload type and includes user data and control data. A numeral in FIG. 4 shows the number of bytes of each field.

However, the payload header is unnecessary in case a GFP frame having the same core header is further classified into plural types and has no hierarchical structure, and the whole payload may be also the information division.

A frame check sequence (FCS) is a field for the error detection of a GFP frame and a value generated in a cyclic redundancy check-32 (CRC-32) is inserted into the field. FCS is an option and this field is not necessarily required.

Figure 5A:
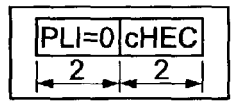
FIGS. 5A and 5B respectively show a format of an idle frame according to GFP.
Figure 5B:
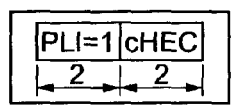

FIG. 5 respectively show a format of an idle frame according to GFP. As shown in FIG. 5, the idle frame includes only a core header. The PLI of a normal idle frame shown in FIG. 5A is '0' and the PLI of an idle frame for a reference channel shown, in FIG. 5B is '1'.

Figure 6:
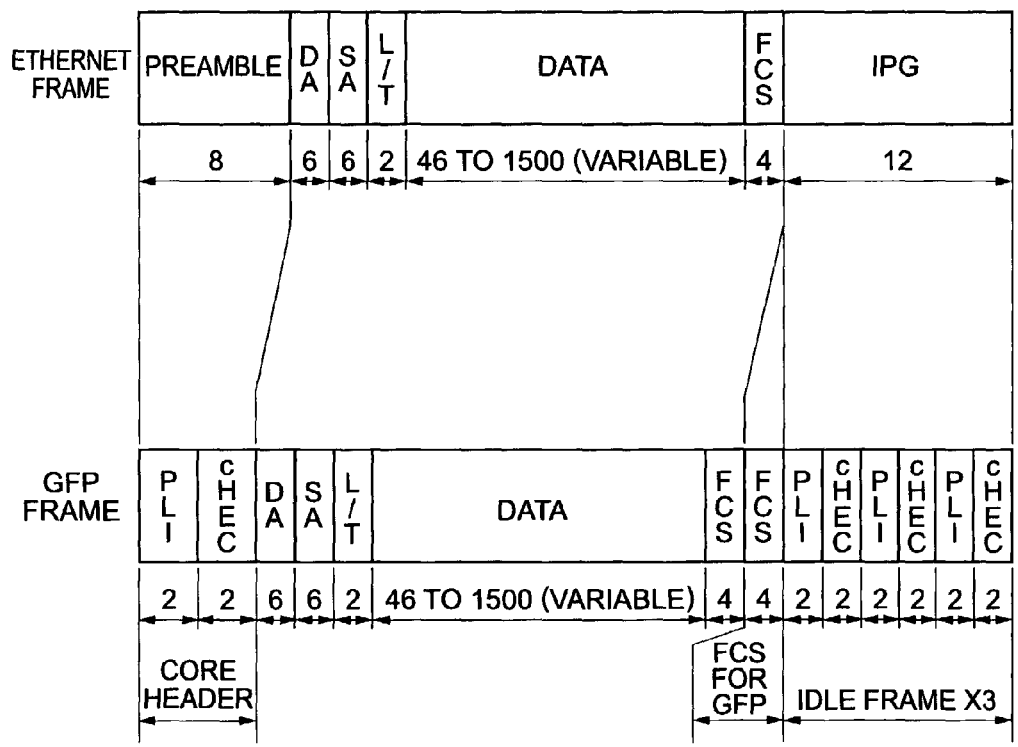
FIG. 6 shows the correspondence of each field in conversion between an Ethernet frame and a GFP frame.

FIG. 6 shows the correspondence of each field in conversion between an Ethernet frame and a GFP frame.

As shown in FIG. 6, an Ethernet frame includes each field of a preamble, DA, SA, L/T, a data division, FCS and IPG.

The preamble is used for detecting a starting point of a frame. DA means a destination address. SA means a source address. L/T (Length/Type) shows the length and the type of a packet. The data division is a field in to which an IP datagram is inserted. A frame check sequence (FCS) is a field used for the error detection of an Ethernet frame. The FCS is different from FCS in an effective frame according to GFP (hereinafter called FCS for GFP). An inter packet gap (IPG) is inserted between frames.

GFP is not required to have hierarchical structure and the payload of a GFP frame includes no payload header.

When an Ethernet frame is converted to a GFP frame, the preamble of the Ethernet frame is removed, fields from DA to FCS are inserted into the payload of the GFP frame, FCS for GFP is calculated and added to be an effective frame. IPG is removed and idle frames of the required number are inserted there.

Next, the operation of the multiplex transmission system according to the first embodiment is described below.

First, the transmitter 1a shown in FIG. 1 receives an Ethernet frame in the channel processing transmitting units 1-1-1, 1-1-2, - - -, 1-1-n via terminals (not shown) and others connected to the input channels 1-11-1, 1-11-2, - - -, 1-11-n. In this case, channels processed by the channel processing transmitting units 1-1-1, 1-1-2, - - -, 1-1-n are called CH1, CH2, - - -, CHn.

The channel processing transmitting units 1-1-1, 1-1-2, 1-1-n remove a preamble of each Ethernet frame, insert fields from DA to FCS into each payload and generate each effective frame according to GFP.

At this time, the Ethernet frame terminating unit 2-1 shown in FIG. 2 terminates the Ethernet frame, extracts each data, the unnecessary data extracting unit 2-2 removes a preamble and IPG from the data, the GFP frame generating unit 2-3 adds a core header and FCS for GFP to the data and generates an effective frame according to GFP.

In this case, as no hierarchical structure is required, the channel processing transmitting units 1-1-1, 1-1-2, - - -, 1-1-n generate no field for a payload header in each payload. Therefore, the length of the Ethernet frame and that of the GFP frame to which the Ethernet frame is converted are equal.

Next, the idle frame inserting units 1-2-1, 1-2-2, - - -, 1-2-n insert an idle frame into each part without the effective frame according to GFP. At this time, the idle frame inserting unit 1-2-1 inserts an idle frame for a reference channel whose PLI is '1'. The idle frame inserting units 1-2-2, - - -, 1-2-n respectively insert a normal idle frame the PLI of which is '1'. As known from FIG. 6, the length of an Ethernet frame and that of an effective frame according to GFP to which the Ethernet frame is converted are equal. Since IPG inserted between Ethernet frames includes at least 12 bytes, three or more idle frames can be necessarily inserted between effective frames, even when a packet in a full band is transmitted. Therefore, in case no hierarchical structure is required for GFP, three or more idle frames can be necessarily secured between effective frames according to GFP without varying a rate.

Next, the multiplexing unit 1-3 multiplexes GFP frames received from each idle frame inserting unit 1-2-1, 1-2-2, - - -, 1-2-n in units of byte by time division.

Next, the framing unit 1-4 inserts data multiplexed by the multiplexing unit 1-3 into a payload of an SDH/SONET frame, generates the SDH/SONET frame and transmits it to the transmission line 1-5.

Next, the receiver 1b receives an SDH/SONET frame from the transmission line 1-5 in its frame synchronizing unit 1-6. The frame synchronizing unit 1-6 is synchronized with the SDH/SONET frame and extracts a payload of the SDH/SONET frame.

Next, the channel identifying unit 1-7 detects a channel including an idle frame for a reference channel the PLI of which is '1' in the payload of the SDH/SONET frame.

The channel identifying unit 1-7 identifies the channel including the idle frame for the reference channel as a reference channel, identifies a byte between a byte of the reference channel and the next byte of the reference channel as a byte of another channel and specifies each channel. The reference channel is CH1 and the succeeding channels are CH2, - - -, CHn.

Further, after the channel identifying unit 1-7 detects channels, it is synchronized with a frame according to GFP of each channel.

Figure 7:
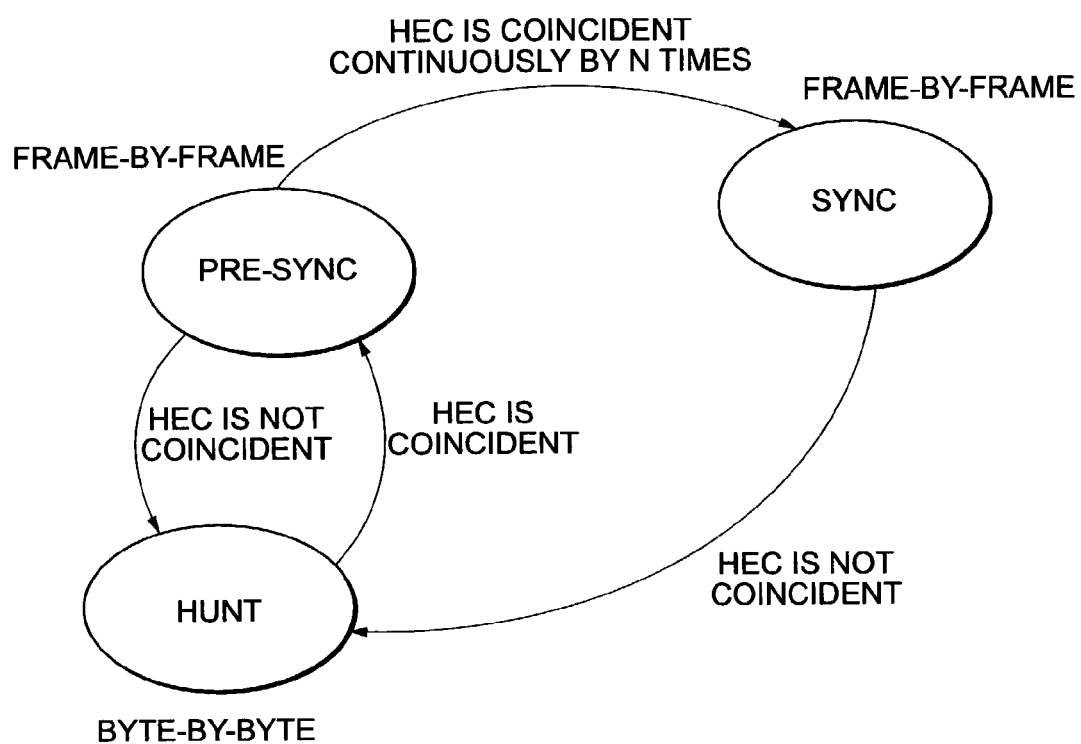
FIG. 7 is a state transition diagram when a channel identifying unit is synchronized with a GFP frame of each channel.

FIG. 7 is a state transition diagram when the channel identifying unit 1-7 is synchronized with a GFP frame of each channel.

A method of synchronizing with a GFP frame will be described below from a viewpoint of one channel.

First, when operation for establishing frame synchronization for a non-synchronized channel is initiated, the channel identifying unit 1-7 makes the channel in a hunt state. In the state in which the channel is hunted, the channel identifying unit 1-7 calculates cHEC for continuous two bytes, sequentially shifting a byte string of the channel every byte and compares the calculated CHEC with cHEC for the succeeding two bytes. When a value of the calculated cHEC and the succeeding two bytes are coincident, the channel identifying unit 1-7 makes the channel a pre-sync state.

In the pre-sync state, the channel identifying unit 1-7 specifies a position of a core header of the next frame based upon a value of PLI and determines whether cHECs are coincident in that position or not. In case cHECs are coincident, the channel identifying unit 1-7 repeats the similar determination until the continuous coincidence of N frames can be verified. A natural number N is set in order to prevent controlled channel from being trapped in a wrong state.

When the coincidence of cHECs in continuous N frames can be verified, the channel identifying unit 1-7 regards frame synchronization as established and makes the channel a sync state.

When GFP frame synchronization is acquired as described above, the channel identifying unit 1-7 notifies the demultiplexing unit 1-8 of a position of each channel.

Next, the demultiplexing unit 1-8 demultiplexes each channel in the position notified from the channel identifying unit 1-7 and transmits to the corresponding idle frame extracting units 1-9-1, 1-9-2, - - -, 1-9-*n*.

Next, the idle frame extracting units 1-9-1, 1-9-2, - - -, 1-9-*n* respectively remove an idle frame from a received signal and respectively transmit only an effective frame to the channel processing receiving units 1-10-1, 1-10-2, - - -, 1-10-*n*.

Next, the channel processing receiving units 1-10-1, 1-10-2, - - -, 1-10-*n* respectively convert the effective frame according to GFP to an Ethernet frame and respectively transmit to terminals (not shown) and others connected to the output channels 1-12-1, 1-12-2, - - -, 1-12-*n*.

At this time, the GFP frame terminating unit 3-1 shown in FIG. 3 terminates the GFP frame and removes a core header and FCS for GFP. The Ethernet frame generating unit 3-2 adds a preamble to the residual data, generates an Ethernet frame, further adds IPG and transmits to the terminal and others.

According to this embodiment, as GFP without hierarchical structure in the payload is used between the transmitter and the receiver, a surplus band is necessarily generated when an Ethernet frame is converted to a GFP frame. As the transmitter inserts the idle frame specific to the reference channel into a surplus band of the reference channel and the receiver detects the reference channel and the other channels based upon the idle frame, channels of the arbitrary number can be efficiently multiplexed by time division according to a standard interface the frame configuration of which is predetermined such as SDH/SONET and each channel is never reduced for a synchronizing signal and a channel identifying signal.

Second Embodiment

Next, a second embodiment of the invention will be described.

Depending upon the type of an inter face of an input/output channel and a method of converting a frame in a channel processing transmitting unit, there is a case that a surplus band is not necessarily created. In that case, an idle frame for identifying a reference channel is required to be transmitted from a transmitter to a receiver according to any method.

A multiplex transmitter never misses a multiplexed position of each channel and a GFP frame as long as the operation normally continues when the multiplex transmitter detects the multiplexed position of each channel and is synchronized with the GFP frame. Therefore, the multiplex transmitter has only to detect a multiplexed position of a channel and to be synchronized with a GFP frame only when the multiplex transmitter misses these because of a fault of a transmission line and others.

Figure 8:
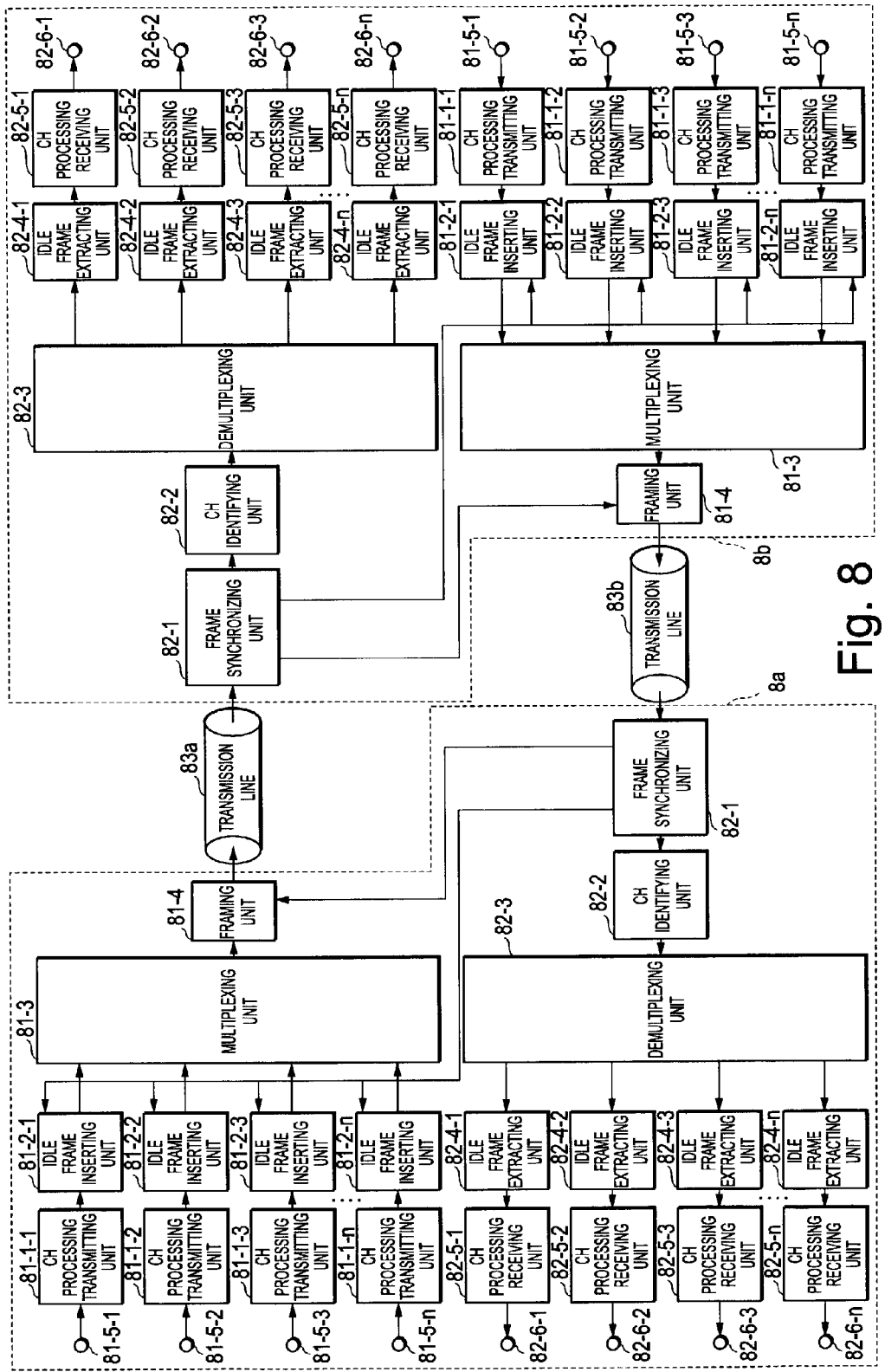
FIG. 8 is a block diagram showing the configuration of a multiplex transmission system equivalent to a second embodiment of the invention.

FIG. 8 is a block diagram showing the configuration of a multiplex transmission system equivalent to the second embodiment of the invention. As shown in FIG. 8, in the multiplex transmission system equivalent to this embodiment, two multiplex transmitters 8*a* and 8*b* that have the same configuration and can transmit and receive a signal multiplexed by time division in an SDH/SONET frame are opposite via transmission lines 83*a* and 83*b*.

The multiplex transmitters 8*a* and 8*b* are respectively provided with channel processing transmitting units 81-1-1, 81-1-2, - - -, 81-1-*n*, idle frame inserting units 81-2-1, 81-2-2, - - -, 81-2-*n*, a multiplexing unit 81-3, a framing unit 81-4, a frame synchronizing unit 82-1, a channel identifying unit 82-2, a demultiplexing unit 82-3, idle frame extracting units 82-4-1, 82-4-2, - - -, 82-4-*n* and channel processing receiving units 82-5-1, 82-5-2, - - -, 82-5-*n*.

The channel processing transmitting units 81-1-1, 81-1-2, - - -, 81-1-*n*, the idle frame inserting units 81-2-1, 81-2-2, - - -, 81-2-*n*, the multiplexing unit 81-3 and the framing unit 81-4 correspond to the channel processing transmitting units 1-1-1, 1-1-2, - - -, 1-1-*n*, the idle frame inserting units 1-2-1, 1-2-2, - - -, 1-2-*n*, the multiplexing unit 1-3 and the framing unit 1-4 respectively in the transmitter 1*a* shown in FIG. 1.

The frame synchronizing unit 82-1, the channel identifying unit 82-2, the demultiplexing unit 82-3, the idle frame extracting units 82-4-1, 82-4-2, - - -, 82-4-*n* and the channel processing receiving units 82-5-1, 82-5-2, - - -, 82-5-*n* correspond to the frame synchronizing unit 1-6, the channel identifying unit 1-7, the demultiplexing unit 1-8, the idle frame extracting units 1-9-1, 1-9-2, - - -, 1-9-*n* and the channel processing receiving units 1-10-1, 1-10-2, - - -, 1-10-*n* respectively in the receiver 1*b* shown in FIG. 1.

However, the multiplex transmitters 8*a* and 8*b* shown in FIG. 8 are different from the corresponding transmitter and receiver shown in FIG. 1 at the following points.

The frame synchronizing unit 82-1 notifies the framing unit 81-4 that a fault of a transmission line is detected when the fault is detected. In SDH/SONET, a fault of a transmission line is equivalent to REC (a receive error).

The frame synchronizing unit 82-1 notifies each idle frame inserting unit 81-2-1, 81-2-2, - - -, 81-2-*n* that an alarm is received when the frame synchronizing unit receives the alarm that a fault of a transmission line is detected from the opposite multiplex transmitter.

The framing unit 81-4 notifies the opposite multiplex transmitter of an alarm that a fault of a transmission line is detected when the framing unit receives a notice that the fault of the transmission line is detected from the frame synchronizing unit 82-1. In SDH/SONET, an alarm that a fault of a transmission line is detected notified the opposite transmitter is equivalent to remote detection indication (RDI).

The idle frame inserting units 81-2-1, 81-2-2, - - -, 81-2-*n* stop each signal from the channel processing transmitting units 81-1-1, 81-1-2, - - -, 81-1-*n* when the idle frame inserting units respectively receive a notice that the alarm is received from the frame synchronizing unit 82-1 and respectively forcedly insert an idle frame into a full band. Until time for transmitting frames equal to/exceeding the number in which frame synchronization can be established on the receive side elapses after the fault of the transmission line recovers, the insertion of idle frames is continued.

The operation of the system when the multiplex transmitter 8*b* shown in FIG. 8 detects REC will be described below.

First, the multiplex transmitter 8*b* that receives an SDH/SONET frame via the transmission line 83*a* detects REC in the frame synchronizing unit 82-1. In the multiplex transmitter 8*b*, the detection of REC is notified from the frame synchronizing unit 82-1 to the framing unit 81-4.

Next, the multiplex transmitter 8*b* notifies the opposite multiplex transmitter 8*a* of RDI by the framing unit 81-4.

The multiplex transmitter 8*a* notifies the idle frame inserting units 81-2-1, 81-2-2, - - -, 81-2-*n* that RDI is received via the frame synchronizing unit 82-1 when the frame synchronizing unit 82-1 receives RDI via the transmission line 83*b*.

Next, the multiplex transmitter 8*a* respectively initiates the insertion of idle frames in the idle frame inserting units 81-2-1, 81-2-2, - - -, 81-2-*n*. The multiplex transmitter 8*a* continues the insertion of idle frames until time for transmitting frames equal to/exceeding the number required for the establishment of frame synchronization elapses after RDI from the multiplex transmitter 8b is stopped. Hereby, the multiplex transmitter 8b can securely detect an idle frame for a reference channel and can detect a multiplexed position of each channel.

Next, the multiplex transmitter 8a terminates the insertion of idle frames in the idle frame inserting units 81-2-1, 81-2-2, - - - , 81-2-n and initiates the transmission of each signal from the channel processing transmitting units 81-1-1, 81-1-2, - - - , 81-1-n.

As the multiple transmitters are also activated in a state in which frame synchronization is not acquired mutually when the operation of the multiplex transmission system is initiated, the multiplex transmitters are operated in the similar way to that in the detection of REC.

In this embodiment, the multiplex transmitter that detects a fault of the transmission line notifies the opposite multiplex transmitter of it and the multiplex transmitter that receives a notice of the fault of the transmission line forcedly inserts idle frames. Therefore, even if there is normally not necessarily a surplus band between effective frames according to GFP, the multiplex transmitter can detect a multiplexed position of a channel when the fault of the transmission line recovers.

According to the invention, the following effect can be acquired. That is, in the invention, the specific idle frame is inserted into a surplus band of a signal of the predetermined input channel on the transmit side and the specific idle frame is detected on the receive side. Hereby, as the number of multiplexed signals and a multiplexed position of each signal are specified, channels of the arbitrary number can be efficiently multiplexed by time division without depending upon the predetermined frame configuration of the transmission line interface and a band of each channel is not reduced for the synchronizing signal and the channel identifying signal.

A surplus band of 20 bytes or more is created by removing the preamble and the inter packet gap of Ethernet. Therefore, as three or more idle frames of 4 bytes can be necessarily inserted between effective frames according to GFP even if the core header of 4 bytes according to GFP and the frame check sequence for GFP of 4 bytes are added, a multiplexed position of each channel can be specified during the transmission of the effective frame in a full band without varying a rate.

Also, in the invention, the receive side that detects a fault of the transmission line notifies the transmit side of it and the transmit side that receives a notice of the fault of the transmission line forcedly inserts the specific idle frame. Therefore, the receive side can detect a multiplexed position of a channel when the fault of the transmission line recovers. As a result, even if a surplus band is not necessarily created in the normal transmission of an effective frame, channels of the arbitrary number can be efficiently multiplexed by time division without depending upon the predetermined frame configuration of the transmission line interface and a band of each signal is not reduced for the synchronizing signal and the channel identifying signal.

While this invention has been described in connection with certain preferred embodiments, it is to be understood that the subject matter encompassed by way of this invention is not to be limited to those specific embodiments. On the contrary, it is intended for the subject matter of the invention to include all alternative, modification and equivalents as can be included within the spirit and scope of the following claims.

What is claimed is:

1. A multiplex transmission system that multiplexes signals of the arbitrary number by time division and transmits a multiplexed signal to a transmission line interface having predetermined frame configuration, wherein:
    the multiplex transmission system comprises:
    a transmitter that converts a signal from each input channel to a frame of a predetermined internal interface, generates an internal signal by inserting a specific idle frame different from an idle frame inserted into a surplus band of a signal of another input channel into a surplus band of a signal of a predetermined input channel, multiplexes internal signals by time division, generates a multiplexed signal and transmits it to the transmission line interface; and
    a receiver that establishes synchronization of the transmission line interface, detects the multiplexed signal, detects the specific idle frame in the multiplexed signal, specifies a position multiplexed by time division of each internal signal based upon a position of the specific idle frame, demultiplexes each internal signal, removes the idle frame or the specific idle frame from each internal signal, restores the predetermined internal interface to the original interface and transmits to each output channel.

2. The multiplex transmission system according to claim 1, wherein:
    the internal interface is GFP.

3. The multiplex transmission system according to claim 2, wherein:
    each interface of the input channel and the output channel is Ethernet; and
    the transmitter converts a signal of Ethernet to GFP by adding a core header according to GFP, a frame check sequence for GFP and a specific idle frame or an idle frame to a surplus band acquired by removing a preamble and an inter packet gap of Ethernet without varying a rate.

4. A multiplex transmission system that multiplexes signals of the arbitrary number by time division and transmits a multiplexed signal to a transmission line interface having predetermined frame configuration, wherein:
    the multiplex transmission system comprises:
    a first device that normally converts a signal from each input channel to a frame of a predetermined internal interface and generates an internal signal, multiplexes internal signals by time division and generates a multiplexed signal, transmits the multiplexed signal to the transmission line interface and inserts a specific idle frame different from an idle frame inserted in place of a signal of another input channel in place of a signal of a predetermined input channel when the first device receives a notice that a fault of a transmission line is detected from an opposite device via the transmission line interface; and
    a second device that is connected to the first device via the transmission line interface, notifies the first device that a fault of a transmission line is detected when the fault is detected, establishes synchronization of the transmission line interface and detects the multiplexed signal when the fault of the transmission line recovers, detects the specific idle frame in the multiplexed signal, specifies a position multiplexed by time division of each internal signal based upon a position of the specific idle frame and demultiplexes the internal signals, removes the idle frame and the specific idle frame from each internal signal, restores the predetermined internal interface to the original interface and transmits to each output channel.

5. The multiple transmission system according to claim 4, wherein:
the internal interface is GFP.

6. The multiple transmission system according to claim 1, wherein:
the transmission line interface is SDH/SONET.

7. The multiple transmission system-according to claim 4, wherein:
the transmission line interface is SDH/SONET.

8. A multiple transmitter that multiplexes signals of the arbitrary number by time division and transmits a multiplexed signal to a transmission line interface having predetermined frame configuration, wherein:
the multiplex transmitter comprises:
a transmitter that converts a signal from each input channel to a frame of a predetermined internal interface, inserts a specific idle frame different from an idle frame inserted into a surplus band of a signal of another input channel into a surplus band of a signal of a predetermined input channel and generates an internal signal, multiplexes internal signals by time division and generates a multiplexed signal and transmits it to the transmission line interface; and
a receiver that establishes synchronization of the transmission line interface, detects the multiplexed signal, detects the specific idle frame in the multiplexed signal, specifies a position multiplexed by time division of each internal signal based upon a position of the specific idle frame and demultiplexes the internal signals, removes the idle frame or the specific idle frame from each internal signal, restores the predetermined internal interface to the original interface and transmits to each output channel.

9. The multiplex transmitter according to claim 8, wherein:
the internal interface is GFP.

10. The multiplex transmitter according to claim 9, wherein:
the interface of a signal is Ethernet; and
the transmitter converts a signal of Ethernet to GFP by adding a core header according to GFP, a frame check sequence for GFP and a specific idle frame or an idle frame respectively into a surplus band acquired by removing a preamble and an interpacket gap of Ethernet without varying a rate.

11. A multiplex transmitter that multiplexes signals of the arbitrary number by time division and transmits multiplexed signals to a transmission line interface having predetermined frame configuration, wherein:
the multiplex transmitter comprises:
a transmitter that normally converts a signal from each input channel to a frame of a predetermined internal interface and generates an internal signal, multiplexes internal signals by time division and generates a multiplexed signal, transmits it to the transmission line interface and inserts a specific idle frame different from an idle frame inserted in place of a signal of another input channel in place of a signal of a predetermined input channel when the transmitter receives a notice that a fault of a transmission line is detected from an opposite receiver via the transmission line interface; and
a receiver that notifies the opposite transmitter that a fault of a transmission line is detected when the fault is detected, establishes synchronization of the transmission line interface when the fault of the transmission line recovers, detects the multiplexed signal, detects the specific idle frame in the multiplexed signal, specifies a position multiplexed by time division of each internal signal based upon a position of the specific idle frame and demultiplexes the internal signals, removes the idle frame and the specific idle frame from each internal signal, restores the predetermined internal interface to the original interface and transmits to each output channel.

12. A multiplex transmitter that multiplexes signals of the arbitrary number by time division and transmits a multiplexed signal to a transmission line interface having predetermined frame configuration, wherein:
the multiplex transmitter comprises:
a channel processing transmitting unit that converts the signal to a frame of a predetermined internal interface;
an idle frame inserting unit that inserts a specific idle frame different from an idle frame inserted into a surplus band of another signal into a surplus band of a predetermined signal and generates an internal signal;
a multiplexing unit that multiplexes internal signals by time division and generates a multiplexed signal; and
a framing unit that transmits the multiplexed signal to the transmission line interface.

13. A multiplex transmitter that receives a signal acquired by multiplexing signals of the arbitrary number by time division from a transmission line interface with predetermined frame configuration, wherein:
the multiplex transmitter comprises:
a frame synchronizing unit that establishes synchronization of the transmission line interface and detects a multiplexed signal acquired by multiplexing internal signals acquired by converting the signals by time division;
a channel identifying unit that detects a specific idle frame in the multiplexed signal and specifies a position multiplexed by time division of each internal signal based upon a position of the specific idle frame;
a demultiplexing unit that demultiplexes the internal signals;
an idle frame extracting unit that removes the idle frame from the internal signals; and
a channel processing receiving unit that restores the internal signal from which the idle frame is extracted to the signal.

14. The multiplex transmitter according to claim 11, wherein:
the internal interface is GFP.

15. The multiplex transmitter according to claim 12, wherein:
the internal interface is GFP.

16. The multiplex transmitter according to claim 13, wherein:
the internal interface is GFP.

17. The multiplex transmitter according to claim 8, wherein:
the transmission line interface is SDH/SONET.

18. The multiplex transmitter according to claim 11, wherein:
the transmitter line interface is SDH/SONET.

19. The multiplex transmitter according to claim 12, wherein:
the transmission line interface is SDH/SONET.

20. The multiplex transmitter according to claim 13, wherein:
the transmission line interface is SDH/SONET.

* * * * *